United States Patent [19]

Russ

[11] 4,184,852
[45] Jan. 22, 1980

[54] METHOD FOR MAKING METHANE FROM METAL CARBIDES

[76] Inventor: James J. Russ, 1702 Tamarack La., Germantown, Tenn. 38138

[21] Appl. No.: 879,777

[22] Filed: Feb. 21, 1978

Related U.S. Application Data

[63] Continuation-in-part of Ser. No. 728,901, Oct. 4, 1976, abandoned, which is a continuation-in-part of Ser. No. 642,891, Dec. 22, 1975, abandoned.

[51] Int. Cl.² ............................................. C10J 3/16
[52] U.S. Cl. ................................... 48/197 R; 48/202; 48/206; 260/449.6 M; 423/439
[58] Field of Search ....................... 48/59, 38, 47, 216, 48/202, 206, 197 R; 106/43; 260/449.6 M, 676 R, 677 R, 449 M; 423/439, 441, 449.6 R; 252/182

[56] References Cited

U.S. PATENT DOCUMENTS

| Re. 22,557 | 10/1944 | Kehl ........................................ 48/38 |
| 555,796 | 3/1896 | Whitehead ............................. 423/439 |
| 1,470,848 | 10/1923 | Karns ....................................... 48/216 |
| 2,686,819 | 8/1954 | Johnson ............................. 260/449 M |
| 2,819,283 | 1/1958 | Montgomery ..................... 260/449.6 |

OTHER PUBLICATIONS

Grant, Hackh's Chemical Dictionary, "Carbide," p. 131, Fourth Edition.

*Primary Examiner*—S. Leon Bashore
*Assistant Examiner*—George C. Yeung
*Attorney, Agent, or Firm*—Elwood S. Kendrick; Patrick F. Bright

[57] ABSTRACT

Methods for making mixtures of hydrocarbons including at least about 85% methane include hydrolyzing at least one metal pseudo-carbide that includes at least one metastable carbide-forming metal element and at least one stable carbide-forming metal element to release methane and the metals, then reforming the pseudo-carbides by reacting the recovered metals with a carbon source such as coal.

11 Claims, 1 Drawing Figure

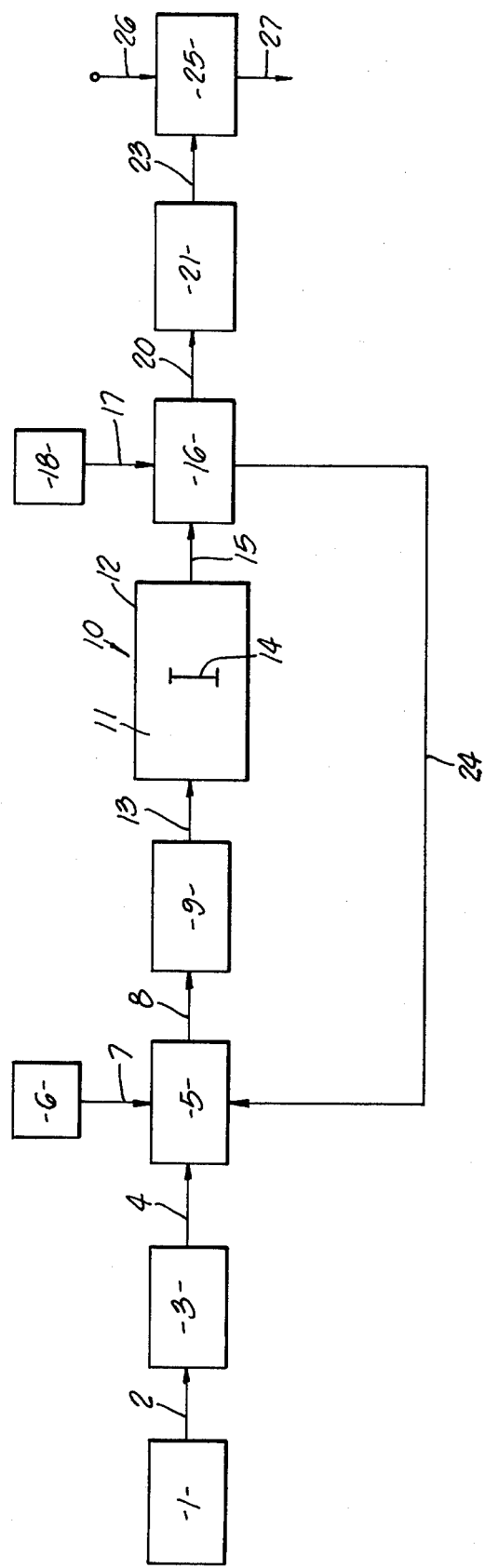

METHOD FOR MAKING METHANE FROM METAL CARBIDES

This application is a continuation-in-part of copending application, U.S. Ser. No. 728,901, filed Oct. 4, 1976, entitled METHOD FOR MAKING METHANE FROM METAL CARBIDES, which is a continuation-in-part of U.S. Ser. No. 642,891, filed Dec. 22, 1975, entitled METHODS FOR MAKING METAL CARBIDES AND FOR MAKING METHANE FROM METAL CARBIDES AND METAL CARBIDE COMPOSITIONS. U.S. Ser. No. 642,891 is now abandoned, but was copending with U.S. Ser. No. 728,901, now abandoned.

This invention relates to methods for making natural gas-type hydrocarbons from metal carbides that comprise at least one metastable and at least one stable carbide-forming metal element.

Metal carbides consisting of a single metal such as calcium carbide, the binary metal carbide of calcium and magnesium, and methods of making these metal carbides are not new. Nor is it new to produce hydrocarbons from such carbides by reacting them with water in the presence of an acid or base catalyst. It is also known to make eutectic mixtures of alloys from metals that can form metal carbides. However, no one has adapted this knowledge to the production of natural gas-type hydrocarbons from carbonaceous materials such as coal using the binary, ternary and quaternary carbides of this invention.

An object of this invention is to provide a method for making metal carbides that may be converted readily to natural gas-type hydrocarbons.

Another object of this invention is to provide metal carbide products that can readily be hydrolyzed to form natural gas-type hydrocarbons and recoverable metal values that may be reconverted to the same or similar metal carbides.

This invention provides a method for making a mixture of hydrocarbons comprising at least about 85% methane comprising reacting water with metal carbides which comprise at least one metastable carbide-forming metal element and at least one stable carbide-forming metal element, and which has the capacity to produce a mixture of gaseous hydrocarbons comprising at least about 85% methane. The metal values produced with the hydrocarbon mixture are substantially recovered and reconverted into these metal carbides which may again be hydrolized to form a hydrocarbon mixture comprising at least 85% methane.

Metastable carbide-forming metal elements have a positive free energy of formation; they absorb energy upon formation of the carbides of this invention from oxides of such metals. Stable carbide-forming metal elements have a negative free energy of formation; they give off energy upon formation of the carbides of this invention from oxides of such metals. The metal carbides may be made by reacting sufficient carbon with a liquid metal alloy comprising at least one metastable carbide-forming metal element and at least one stable carbide-forming metal element. Where metastable and stable carbide-forming metal elements are not available in pure or relatively pure form, metal carbides used in the new process may be made from at least one compound of at least one metastable carbide-forming metal element and at least one compound of at least one stable carbide-forming metal element, usually from oxygen-containing compounds of such metals, by reducing these compounds with sufficient carbon to form such carbides, thus forming first a liquid metal alloy, and then a carbide comprising at least one metastable and at least one stable carbide-forming metal element each. Preferably, these two steps are effected in a single vessel at a temperature in the range of not more than about 2200° F., and at pressures in the range of about 0.5 to about 2 atmospheres, preferably about one atmosphere.

At these temperatures and pressures, and with the employment of at least one stable carbide-forming metal element and at least one metastable carbide-forming metal element, true metal carbides of the kind set forth in Whitehead, U.S. Pat. Ser. No. 555,796, do not form. Thus, Whitehead's true carbides form at much higher temperatures than 2200° F. Rather, the metastable/stable metal carbide complexes of this invention form. In such complexes, the carbon content is typically lower than that required to satisfy the sum of the valences of the metals therein, but is combined with the metals in a highly reactive form. Such complexes readily dissociate upon hydrolysis to form a gas mixture comprising at least about 85% methane and compounds selected from the group consisting of oxides and hydroxides of the metastable metals and stable metals in the complexes. Because the heats of formation of these carbides are considerably lower than the sum of the BTU content of the gas mixtures formed upon hydrolysis and the heat released by the hydrolysis process itself, the method of this invention produces a natural gas substitute from carbonaceous materials such as coal at economically attractive costs.

The carbides of this invention must contain at least one metastable, and at least one stable carbide-forming metal element each. Examples of the stable carbide-forming metal elements are aluminum, manganese, calcium, magnesium, beryllium, and boron. Examples of the metastable carbide-forming metal elements are cadmium, zinc, barium, copper, zirconium, titanium, chromium, iron and lead. Reacted with carbon, these metals may form binary, ternary or quaternary metal carbides, or a mixture of two or more of these carbides, provided at least one stable, and at least one metastable carbide-forming metal element is present in the combination. Typically, the stable metal or metals form higher mole percentages in these carbide complexes than do the metastable metal or metals. Typical binary combinations include: Aluminum-zinc ($Al_4.Zn_2.C_3$), aluminum-zirconium ($Al_4.Zr_2.C_3$), manganese-iron ($Mn_7.Fe_7.C_3$), the calcium-zirconium ($Ca_2.Zr_2.C_4$). Examples of ternary combinations are: Aluminum-beryllium-zinc ($Al_4.Be_4.Zn_2.C_3$), boron-zinc-aluminum ($B_2.Zn_2.Al_4.C_3$), aluminum-zinc-titanium ($Al_4.Zn_2.Ti_2.C_3$), aluminum-zinc-boron ($Al_4.Zn_2.B_2.C_3$) and beryllium-zinc-boron ($Be_4.Zn_2.B_2.C_3$). Examples of quaternary combinations are: Aluminum-zinc-beryllium-lithium ($Al_4.Zn_2.Be_4.Li_2.C_3$), aluminum-zinc-titanium-magnesium ($Al_4.Zn_2.Ti_2.Mg_2.C_3$), aluminum-zinc-titanium-lithium ($Al_4.Zn_2.Ti_2.Li_2.C_3$), cadmium-lead-zinc titanium ($Cd_4.Pb_2.Zn_2.Ti_2.C_3$) and cadmium-zinc-titanium-beryllium ($Cd_4.Zn_2.Ti_2.Be_4.C_3$). In the iron-manganese binary system, the manganese content may be from 3 to 23 atoms, the iron content, from 1 to 7 atoms, and the carbon content may be 2 or 3 atoms. As the number of manganese atoms in the system increases, the number of iron atoms in the system will also increase.

The carbon used to form the metal carbides for this process may be obtained from any suitable carbonaceous source such as hydrocarbons and carbon-containing compounds such as coke, coals, and mixtures of any two of these sources. In the presently preferred embodiment, coal is the carbon source.

In the process of this invention, the carbon potential of the carbides is converted to a hydrocarbon mixture comprising at least 85% methane by reaction with water.

In a preferred embodiment, the metal carbide is fed to a hydrolyzer jacketed at least partially by water circulating pipes, and water is sprayed onto the carbide to form methane, other hydrocarbons and metal compounds. The reactant water may flow at a rate in the range of about 20 to about 2,400 gallons per hour, and the metal carbides at a rate of about 3,600 pounds to about 336,000 pounds per hour. The reaction is exothermic, and the hydrolyzer is maintained at a maximum temperature of about 350° F. by circulating water through the pipes jacketing the reactor. Thus, where the heat of reaction is as high as 1100° F., the water coolant is converted to steam at a rate in the range of about 500 to about 50,000 gallons per hour. This steam may be used as a heat source as such, or converted to other forms of energy in known ways.

Hydrolysis of the metal carbides produces a mixture of hydrocarbons ocmprising at least about 85% and preferably about 90% methane, together with such other hydrocarbons as ethane, ethylene, propylene, and acetylene, and metal oxides and hydroxides of stable and metastable carbide-forming metal elements. These metal values may be recovered and used to make additional metal carbides. The hydrocarbonaceous gases produced may contain contaminants such as hydrogen sulfide which may be removed by well-known methods. Typically, the pressure of the hydrocarbonaceous gases produced in the hydrolyzer must be increased, say, from a pressure in the range of about 2 to about 8 pounds, to a pressure in the range of about 40 to about 1,500 pounds for industrial or commercial uses. These gases may also require dilution with active or inert diluents such as oxides of carbon and nitrogen, respectively, to bring the BTU gas value to conformance with delivered pipeline gases, normally 950 BTU/SCF.

Because the preferred embodiment of this invention contemplates reduction of metal compounds such as hydroxides and oxides with carbon to form binary, ternary and quaternary liquid metal alloys and carbides, most impurities such as sulfur, sulfur compounds and silica may be readily removed as a slag which forms atop the liquid metal and alloys thereof so produced. Little oxides of sulfur is formed in this embodiment, precluding the need to prevent their escape or to effect their recovery, as is necessary in direct coal gasification processes. Thus, this invention is particularly suited to the gasification of coals that would produce more than say, 20 parts per million of sulfur dioxide upon combustion. Some hydrogen sulfide is formed, but is readily removed by scrubbing the hydrocarbons produced during formation of the metal carbides. Advantageously, all steps in the process are effected at pressures close to atmospheric. Moreover, except for the method for forming metal carbides, these processes are mildly or strongly exothermic, so that the overall consumption of energy used to produce hydrocarbons is substantially smaller than the energy value of the hydrocarbons produced. Most of the metal values used to make the metal carbides are recovered from the hydrolysis of the carbides, and may be reconverted to metal carbides.

Referring now to the drawing, which illustrates by block diagram the preferred practice of this invention, coal or other carbonaceous material from source 1 passes by line 2 to low-pressure crusher 3 where the carbonaceous material is reduced to sizes that may be handled efficiently. The crushed coal passes via line 4 to briquetter 5 where the coal is mixed with at least one metastable carbide-forming metal element, at least one compound of such an element, or a combination thereof, and at least one stable carbide-forming metal element, at least one compound of such an element, or a combination thereof, entering briquetter 5 from source 6 via line 7. The resulting mixture is formed into briquettes that contain at least a sufficient amount of carbon to reduce whatever stable and metastable compounds are present to the metal elements thereof, and to convert the metals to the carbides used in the process of the invention. These briquettes pass via line 8 to heating zone 9 where sufficient heat is supplied to expel a substantial portion, preferably substantially all, of the water from the briquettes.

From heating zone 9, the relatively dry briquettes pass to reactor-synthesizer 10, which contains reactor zone 11 and synthesizer zone 12. Pellets enter reactor zone 11 via line 13, and are subjected there to a temperature in the range of about 1400° F. to about 2200° F., and to near atmospheric pressure, and are reduced to a mixture of metastable and stable carbide-forming metal elements, together with some carbides of these metal elements. The liquid mixture passes below baffle 14 in reactor-synthesizer 10 into synthesizer zone 12, and carbon monoxide, hydrogen and other gases produced in reactor zone 11 pass above baffle 14 into synthesizer zone 12. In synthesizer zone 12, at least sufficient carbon, in the form of carbon monoxide or otherwise, is present to form a metal carbide comprising at least one metastable carbide-forming metal element and at least one stable carbide-forming metal element. That carbide, together with excess carbon, if any, passes to hydrolyzer 16 via line 15.

In hydrolyzer 16, metal carbides are sprayed with water, with or without acid or base catalyst as an initiator of the reaction, entering hydrolyzer 16 via line 17 from source 18. Coolant water passes through pipes (not shown) jacketing hydrolyzer 16, and heat of the hydrolysis reaction converts the water to steam which exits via line 19. Hydrocarbon gases produced pass via line 20 to scrubber 21 where hydrogen sulfide and other contaminants, if any, are removed, and then via line 23 to compressor zone 25 where diluent, if desired, is added via line 26. Hydrocarbon gases of the proper pressure and concentration pass from zone 25 via line 27 to consumers.

Metal compounds produced in the hydrolyzer 16 pass via line 24 to briquetter 5 where they are combined with makeup metal compounds and metal elements from source 6, and are reconverted to metal carbides as described above.

Little metal value is lost in the preferred embodiment, and methane and other hydrocarbons are produced at low pressure, relative mild temperatures, and with no sulfur oxides emitted to the atmosphere. Minor attrition of metal values does occur, but only carbonaceous metarial is consumed in substantial quantities. Even the water used for cooling the hydrolyzer may be recovered and reused without any purification or other treatment.

EXAMPLE I

385 Grams of sugar were pyrolized at 350° F. in a Kress furnace to produce carbon char. 13.9 Grams of the carbon char was mixed with 279.6 grams of aluminum, 332.1 grams of zinc, and 343.1 grams of manganese, the mixture was placed in a Tercod crucible, and heated to 900° C. under an Argon gas flow of about 2 to about 3 cubic feet per hour. The mixture was stirred with an aluminum rod to eliminate the formation of any wetting barrier during this heating step.

The resulting carbide product was removed from the crucible after three hours holding time and allowed to cool. A 5.32 gram sample was prepared from the bulk product, crushed, and placed in an extraction thimble contained in the neck of a flask fitted with an air condenser. 50 Grams of mercury were added to the thimble, and the flask system was placed on a hot plate with an exhaust line venting the top of the condenser. The mercury was refluxed for a four hour period, and thereafter the system was cooled, and the sample weighed. The net weight of the sample was 4.07 grams. The analysis of the carbide was as follows: zinc and manganese—27.6%, aluminum, 45.3%; combined carbon, 19.6% (by difference); and free carbon, 7.5%. The empirical formula of the carbide was:

$$\text{Aluminum}_{1.02}(\text{Zinc}+\text{Manganese})_{0.26}\text{Carbon}$$

The 4.07 gram-sample was transferred to a hydrolysis container and treated with 200 milliliters of 5% HCl in water. The gas evolved was collected in an inverted cylinder on a water bath, and transferred to a 10 cc gas cell for infrared spectral analysis, 1.5 liters of gas evolved.

The evolved gas was analyzed on a Beckman Acculab VI Spectrophotometer, and the product was seen to comprise methane as the principal constituent with traces of ethylene and carbon monoxide also present. The gas produced contained about 90% to about 95% methane and no acetylene.

EXAMPLE II

Carbon char was prepared from sugar as described in Example I above. Thereafter, 1,468 grams of the char were mixed with 1,508 grams of magnesium, 1,580 grams of iron, and 2,313 grams of manganese. The mixture was heated in the Kress furnace at 1100° C. under an Argon flow at the rate of about 3 cubic feet per hour. During the heating, the mixture was stirred with a steel rod. Heating was continued for five hours, and thereafter the mixture was recovered and cooled. An analysis of the carbide showed the following: Iron, 33.6%; manganese plus carbon, 63.0%; free carbon, 3.4%; and magnesium, zero percent. Under the test conditions, magnesium fumed off and did not combine or alloy.

A five gram sample of the carbide produced in this example was placed in the hydrolysis chamber, and treated with 200 milliliters of a 5% solution of hydrogen chloride in water. Approximately 2.3 liters of gas evolved, and were collected in an inverted cylinder in a water bath, as described in Example I above.

The gas produced was analyzed on a Beckman Acculab VI Spectrophotometer, and observed to include at least about 85% methane, and lesser amounts of ethane, ethylene and carbon monoxide. Again, no acetylene was produced.

What is claimed is:

1. A method for making methane comprising reacting sufficient water with a metal carbide complex which comprises a mixture of at least one metastable carbide-forming metal element selected from the group consisting of cadmium, zinc, barium, copper, zirconium, iron and lead and at least one stable carbide forming metal element selected from the group consisting of aluminum, manganese, calcium, magnesium, beryllium, and boron, to produce a mixture of gaseous hydrocarbons comprising at least about 85% methane and recoverable metal values comprising a mixture of said at least one metastable carbide-forming metal element and said at least one stable carbide-forming metal element, then reacting said recovered metal values with sufficient carbon to form said metal carbide complex.

2. The method of claim 1 wherein said metal carbide complex comprises one metastable carbide-forming metal element and one stable carbide-forming metal element.

3. The method of claim 2 wherein the metal carbide complex consists of zinc, aluminum and carbon.

4. The method of claim 2 wherein the metal carbide complex consists of iron, manganese and carbon.

5. The method of claim 1 wherein the metal carbide complex has the capacity to produce a mixture of hydrocarbons comprising at least about 90% methane.

6. The method of claim 1 wherein said metal carbide complex is made by reacting a mixture of at least one compound of the at least one metastable carbide-forming metal element with at least one compound of at least one stable carbide-forming metal element, and with sufficient carbon to reduce said mixture of compounds to form said metal carbide complex.

7. A method for making methane comprising forming at least one metal carbide complex by reducing a mixture of; at least one metastable carbide-forming metal element selected from the group consisting of cadmium, zinc, barium, copper, zirconium, iron and lead and at least one stable carbide-forming metal element selected from the group consisting of aluminum, manganese, calcium, magnesium, beryllium, and boron with sufficient carbon at a temperature of not more than about 2200° F. and a pressure of not more than about 2 atmospheres to form said complex, hydrolyzing said at least one metal carbide complex to form compounds comprising a mixture of said at least one metastable carbide-forming metal element and said at least one stable carbide-forming metal element, said compounds selected from the group consisting of oxides and hydroxides thereof, and a gas mixture comprising at least about 85% methane by volume, and then forming said at least one metal carbide complex from said compounds.

8. The method of claim 7 wherein said at least one metal carbide complex includes carbon derived from coal.

9. The method of claim 8 wherein said coal comprises sufficient sulfur to produce more than 20 parts per million of sulfur dioxide upon combustion.

10. The method of claim 7 wherein said metal carbide complex comprises one metastable carbide-forming metal element and one stable carbide-forming metal element.

11. The method of claim 10 wherein the metal carbide complex consists of zinc, aluminum and carbon.

* * * * *